(12) United States Patent
Sun

(10) Patent No.: US 11,992,836 B2
(45) Date of Patent: May 28, 2024

(54) MICROFLUIDIC DEVICE AND METHOD FOR MANUFACTURING THE SAME, AND METHOD AND SYSTEM FOR DETECTING THE NUMBER OF BIOMOLECULES

(71) Applicants: Beijing BOE Technology Development Co., Ltd., Beijing (CN); BOE TECHNOLOGY GROUP CO., LTD., Beijing (CN)

(72) Inventor: Tuo Sun, Beijing (CN)

(73) Assignees: Beijing BOE Technology Development Co., Ltd., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 756 days.

(21) Appl. No.: 17/272,371

(22) PCT Filed: Jun. 16, 2020

(86) PCT No.: PCT/CN2020/096273
§ 371 (c)(1),
(2) Date: Mar. 1, 2021

(87) PCT Pub. No.: WO2020/259347
PCT Pub. Date: Dec. 30, 2020

(65) Prior Publication Data
US 2021/0322977 A1    Oct. 21, 2021

(30) Foreign Application Priority Data
Jun. 25, 2019 (CN) .......................... 201910553499.1

(51) Int. Cl.
*G01N 33/68* (2006.01)
*A01N 1/02* (2006.01)
(Continued)

(52) U.S. Cl.
CPC .... *B01L 3/502707* (2013.01); *G01N 15/0656* (2013.01); *G01N 33/54373* (2013.01);
(Continued)

(58) Field of Classification Search
CPC ........... B01L 3/502707; B01L 2200/12; B01L 2300/08; B01L 2300/12; G01N 15/0656;
(Continued)

(56) References Cited

U.S. PATENT DOCUMENTS 6,445,271 B1  9/2002 Johnson
6,930,292 B1  8/2005 Winther
(Continued)

FOREIGN PATENT DOCUMENTS

CN   1452718 A    10/2003
CN   101300472 A  11/2008
(Continued)

OTHER PUBLICATIONS

China Patent Office, First Office Action dated Dec. 4, 2020, for corresponding Chinese application 201910553499.1.

*Primary Examiner* — Jennifer Wecker
*Assistant Examiner* — Oyeleye Alexander Alabi
(74) *Attorney, Agent, or Firm* — HOUTTEMAN LAW LLC

(57) ABSTRACT

The present disclosure provides a microfluidic device and a manufacturing method therefor, and a method for detecting the number of biomolecules and a system for detecting the number of biomolecules. The microfluidic device includes a glass substrate; a plurality of first metal strips formed on the glass substrate; a photoresist covering the plurality of first metal strips; a fluid cavity formed in the photoresist; a plurality of second metal strips formed on the photoresist, wherein a head end of one first metal strip and a tail end of the other first metal strip in any adjacent two first metal (Continued)

strips are electrically coupled through a head end and a tail end of one second metal strip between the two first metal strips, so that the plurality of first metal strips and the plurality of second metal strips form a hollow inductor structure around the fluid cavity.

20 Claims, 4 Drawing Sheets

(51) Int. Cl.
*B01L 3/00* (2006.01)
*C07C 309/65* (2006.01)
*C07C 309/73* (2006.01)
*F04B 43/12* (2006.01)
*G01N 1/40* (2006.01)
*G01N 15/06* (2024.01)
*G01N 21/33* (2006.01)
*G01N 21/64* (2006.01)
*G01N 33/52* (2006.01)
*G01N 33/543* (2006.01)
*G01N 35/10* (2006.01)
*G03F 7/20* (2006.01)
*G03F 7/26* (2006.01)

(52) U.S. Cl.
CPC ....... *B01L 2200/12* (2013.01); *B01L 2300/08* (2013.01); *B01L 2300/12* (2013.01); *G03F 7/2022* (2013.01); *G03F 7/26* (2013.01)

(58) Field of Classification Search
CPC ......... G01N 33/54373; G01N 15/1023; G01N 27/026; G01N 33/588; G01N 2015/1006; G01N 15/1031; G01N 15/10; G03F 7/2022; G03F 7/26
See application file for complete search history.

(56) References Cited

U.S. PATENT DOCUMENTS

| | | |
|---|---|---|
| 2003/0143639 A1 | 7/2003 | Matsushita et al. |
| 2009/0079963 A1 | 3/2009 | Ermantraut et al. |
| 2013/0119440 A1* | 5/2013 | Ackerson ........... G01N 27/4145 257/253 |
| 2013/0193003 A1 | 8/2013 | Reed et al. |

FOREIGN PATENT DOCUMENTS

| | | | | |
|---|---|---|---|---|
| CN | 102141532 A | | 8/2011 | |
| CN | 202002870 U | | 10/2011 | |
| CN | 103080737 A | | 5/2013 | |
| CN | 104069905 A | | 10/2014 | |
| CN | 106483284 A | | 3/2017 | |
| CN | 107497507 A | | 12/2017 | |
| CN | 108507910 A | | 9/2018 | |
| CN | 109092379 A | | 12/2018 | |
| CN | 109092379 A | * | 12/2018 | ........ B01L 3/502792 |
| CN | 208642692 U | | 3/2019 | |
| CN | 109590037 A | | 4/2019 | |
| CN | 110227565 A | | 9/2019 | |
| EP | 0535479 A1 | | 4/1993 | |
| EP | 1146331 A1 | | 10/2001 | |
| WO | WO0107890 A2 | | 2/2001 | |
| WO | WO2008030395 A1 | | 3/2008 | |

* cited by examiner

MICROFLUIDIC DEVICE AND METHOD FOR MANUFACTURING THE SAME, AND METHOD AND SYSTEM FOR DETECTING THE NUMBER OF BIOMOLECULES

CROSS REFERENCE TO RELATED APPLICATIONS

The present application claims the priority of the Chinese Patent Application No. 201910553499.1 filed on Jun. 25, 2019, the content of which is incorporated herein by reference in its entirety.

TECHNICAL FIELD

The present disclosure relates to the field of biological detection, and in particular, relates to a microfluidic device and a method for manufacturing a microfluidic device, a method and a system for detecting the number of biomolecules.

BACKGROUND

The use of a microfluidic device for analysis of a number/concentration of target biomolecules has become a common analytical means in modern medicine. However, after a common microfluidic device is calibrated, a number representation is usually performed by adopting an optical test method, which needs a large-scale equipment such as a fluorescence microscope, so that a portability/a convenience in use and the like of the device are reduced, and a cost for testing an equipment is stayed at a high level, and a long-term maintenance is inconvenient.

SUMMARY

The present disclosure provides a microfluidic device and a method for manufacturing a microfluidic device, and a method and a system for detecting a number of biomolecules.

The microfluidic device of the present disclosure includes:
  a glass substrate;
  a plurality of first metal strips arranged in a first direction and on the glass substrate;
  a photoresist extending along the first direction, which covers the plurality of first metal strips and exposes a head end and a tail end of each of the first metal strips;
  a fluid cavity extending in the first direction and formed in the photoresist;
  a plurality of second metal strips formed on the photoresist, wherein the plurality of second metal strips extend over an upper surface of the photoresist, and continuously extend along sidewalls of the photoresist to the glass substrate, to form respective head ends and tail ends, and wherein orthographic projections of the plurality of second metal strips on the glass substrate are arranged along the first direction, the head end of one first metal strip and the tail end of the other first metal strip in any adjacent two first metal strips are electrically coupled through the head end and the tail end of one second metal strip between the two first metal strips, so that the plurality of first metal strips and the plurality of second metal strips form a hollow inductor structure around the fluid cavity, and the hollow inductor structure is provided with a first electrode and a second electrode for an external connection;
  a liquid inlet and a liquid outlet formed at both ends of the photoresist in the first direction, and in liquid communication with the fluid cavity.

In an embodiment, in the first direction, the head end of the first one of the plurality of second metal strips is used as the first electrode of the hollow inductor structure, the tail end of the $n^{th}$ one of the plurality of second metal strips is electrically coupled with the head end of the $n^{th}$ one of the plurality of the first metal strips, the tail end of the $n^{th}$ one of the plurality of the first metal strips is electrically coupled with the head end of the $(n+1)^{th}$ one of the plurality of the second metal strips, the tail end of the $N^{th}$ one of the plurality of the second metal strips is electrically coupled with the head end of the $N^{th}$ one of the plurality of the first metal strips, and the tail end of the $N^{th}$ one of the plurality of the first metal strips is used as the second electrode of the hollow inductor structure,
  where N is the number of the plurality of the first metal strips or the plurality of the second metal strips, N and n are natural numbers, and satisfy $1 \leq n \leq N-1$.

In an embodiment, the plurality of first metal strips are parallel to each other and extend along a second direction; the plurality of second metal strips are parallel to each other and extend along a third direction,
  wherein an included angle between the second direction and the third direction is an acute angle.

In an embodiment, each of an included angle between the second direction and the first direction and an included angle between the third direction and the first direction is an acute angle or an obtuse angle.

In an embodiment, the fluid cavity is spaced from the glass substrate by a distance.

In an embodiment, the microfluidic device further includes a sacrificial colloid formed on the photoresist, made of a material different from that of the photoresist, covering the photoresist and extending onto the glass substrate; the fluid cavity is formed in the photoresist; the liquid inlet and the liquid outlet are formed in the sacrificial colloid; and the plurality of second metal strips are formed on an upper surface of the sacrificial colloid.

In an embodiment, a cross section of the photoresist perpendicular to an extending direction of the photoresist is of a trapezoidal shape.

In an embodiment, the fluid cavity is formed in a middle area of a surface of a side of the photoresist distal to the glass substrate.

In an embodiment, a patterned metal film is formed on an inner surface of the fluid cavity.

The method for manufacturing a microfluidic device of the present disclosure includes:
  forming a plurality of first metal strips electrically insulated from each other and arranged along a first direction on the glass substrate,
  forming a photoresist extending along the first direction, to cover the plurality of first metal strips and expose a head end and a tail end of each first metal strip;
  forming a fluid cavity extending along the first direction in the photoresist;
  forming a plurality of second metal strips on the photoresist, so that the plurality of second metal strips extend over an upper surface of the photoresist and continuously extend along two sidewalls of the photoresist to the glass substrate to form respective head ends and tail ends, orthographic projections of the plurality of second metal strips on the glass substrate are arranged along the first direction, the head end of one first metal strip and the tail end of the other first metal strip in any adjacent two first metal strips are electrically coupled through the head end and the tail end of one second metal strip between the two first metal strips, so that the plurality of first metal strips and the plurality of second metal strips form a hollow inductor structure around the fluid cavity; and forming a liquid inlet and a liquid outlet at both ends of the photoresist in the first direction, which are communicated to the fluid cavity.

In an embodiment, the forming the fluid cavity extending along the first direction in the photoresist and the forming the plurality of second metal strips on the photoresist include:

exposing a part in the photoresist for preforming the fluid cavity;

forming a sacrificial colloid covering the photoresist and the exposed head end and the exposed tail end of each first metal strip;

exposing and developing the sacrificial colloid at positions covering the head end and the tail end of each first metal strip and the sacrificial colloid at positions, where the liquid inlet and the liquid outlet are to be formed, at two ends of the photoresist in the first direction, such that the head end and the tail end of each first metal strip are exposed, and the liquid inlet and the liquid outlet are formed, forming a plurality of second metal strips arranged along the first direction and electrically insulated from each other on the sacrificial colloid, so that the plurality of second metal strips extend over an upper surface of the sacrificial colloid and continuously extend along sidewalls of the sacrificial colloid to the glass substrate to form respective head ends and tail ends, and the head end and the tail end of each second metal strip are electrically coupled with the tail end of one first metal strip and the head end of the other first metal strip in corresponding two first metal strips to which the second metal strip extends, developing the photoresist at the exposed position for preforming the fluid cavity, to form the fluid cavity extending along the first direction, wherein a hollow inductor structure is formed by the plurality of first metal strips and the plurality of second metal strips surrounding the fluid cavity.

In an embodiment, the forming the fluid cavity extending along the first direction in the photoresist and the forming the plurality of second metal strips on the photoresist include:

exposing and developing a part in the photoresist for preforming the fluid cavity, to form the fluid cavity extending along the first direction;

forming a patterned metal film in the fluid cavity;

forming a sacrificial colloid covering the photoresist and the exposed head end and the exposed tail end of each first metal strip;

exposing and developing the sacrificial colloid at positions covering the head end and the tail end of each first metal strip and the sacrificial colloid at positions, where the liquid inlet and the liquid outlet are to be formed, at two ends of the photoresist in the first direction, such that the head end and the tail end of each first metal strip are exposed, and the liquid inlet and the liquid outlet are formed, forming a plurality of second metal strips arranged along the first direction and electrically insulated from each other on the sacrificial colloid, so that the plurality of second metal strips extend over an upper surface of the sacrificial colloid and continuously extend along sidewalls of the photoresist to the glass substrate to form respective head ends and tail ends, and the head end and the tail end of each second metal strip are electrically coupled with the tail end of one first metal strip and the head end of the other first metal strip in corresponding two first metal strips to which the second metal strip extends, wherein a hollow inductor structure is formed by the plurality of first metal strips and the plurality of second metal strips surrounding the fluid cavity.

In an embodiment, the photoresist and the sacrificial colloid are developed with different developing solutions.

The system for detecting a number of biomolecules of the present disclosure includes:

a controller;

a signal source coupled to the controller;

a voltmeter coupled to the controller;

a variable capacitor coupled to the controller, the signal source and the voltmeter;

the microfluidic device as described above, wherein, the first electrode of the hollow inductor structure of the microfluidic device is electrically coupled with a first electrode of the variable capacitor, and the second electrode of the hollow inductor structure is electrically connected with a second electrode of the variable capacitor;

the controller is configured to adjust a frequency of the signal source to resonate the hollow inductor structure and the variable capacitor;

the voltmeter is configured to determine whether a resonance is achieved or not through a displayed voltage value across the first electrode and the second electrode of the variable capacitor.

In an embodiment, the variable capacitor is manufactured on a flexible printed circuit board.

The method for detecting a number of biomolecules using the system as described above includes:

modifying the fluid cavity with an antigen or an antibody;

adjusting the frequency of the signal source to resonate the hollow inductor structure and the variable capacitor;

causing a liquid to be tested containing a target substance to enter the fluid cavity from the liquid inlet and to flow out from the liquid outlet, so that the antigen or the antibody in the fluid cavity is combined with the target substance and leaving remained in the fluid cavity;

introducing markers with magnetic quantum dots into the fluid cavity, so that they are combined with the target substance in the fluid cavity, thereby resulting in a change in an inductance value of the hollow inductor structure;

adjusting a capacitance value of the variable capacitor to resonate the hollow inductor structure and the variable capacitor resonate again;

obtaining a changed inductance value from the adjusted capacitance value and the frequency of the resonance; and obtaining the number of biomolecules of the target substance according to the inductance value.

In an embodiment, the magnetic quantum dot is $Fe_3O_4$.

BRIEF DESCRIPTION OF DRAWINGS

Embodiments of the present invention will be described in detail below with reference to the accompanying drawings, in which.

DETAIL DESCRIPTION OF EMBODIMENTS

Figure 1:
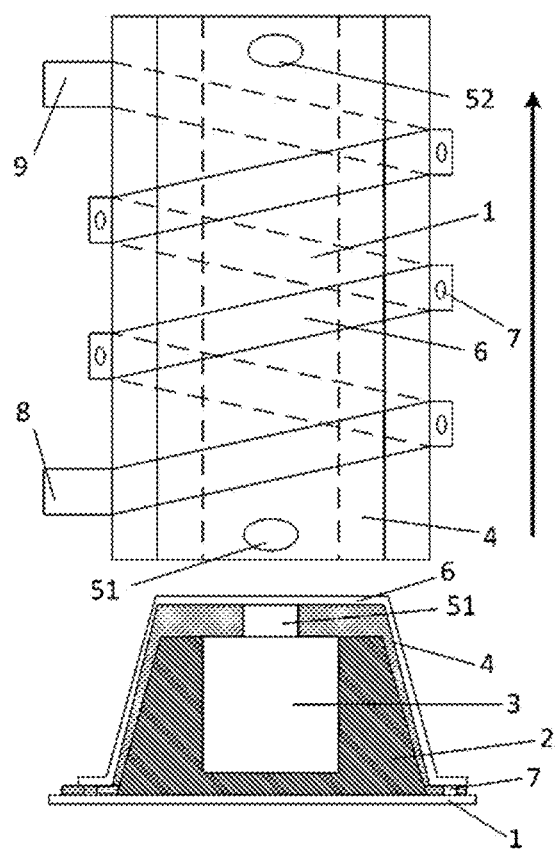
FIG. 1 shows a schematic top view and a cross-sectional view of a structure of a microfluidic device according to an embodiment of the present disclosure.

To more clearly illustrate the present disclosure, the present disclosure is further described below in conjunction with preferred embodiments and the drawings. Similar components in the drawings are denoted by a same reference sign. It is to be understood by one of ordinary skill in the art that the following detailed description is illustrative and not restrictive, and is not to be taken as limiting the scope of the present disclosure.

As shown in FIG. 1, FIG. 1 is a top view and a corresponding front cross-sectional view of a structure of a microfluidic device according to an embodiment of the present disclosure, wherein an upper view is the top view, and a lower view is a schematic diagram of only a part of elements. The microfluidic device includes:

a glass substrate (not shown in the figures);

a plurality of first metal strips 1 arranged in a first direction and formed on the glass substrate;

a photoresist 2 extending along the first direction, which covers the plurality of first metal strips 1 and exposes a head end and a tail end of each first metal strip 1;

a fluid (flow channel) cavity 3 extending in the first direction and formed in the photoresist 2;

a plurality of second metal strips 6 arranged along the first direction and formed on the photoresist 2, wherein the plurality of second metal strips 6 extend over an upper surface of the photoresist 2, and continuously extend along sidewalls of the photoresist 2 to the glass substrate, to form respective head ends and tail ends, and wherein the head end of one first metal strip and the tail end of the other first metal strip in any adjacent two first metal strips 1 are electrically coupled through the head end and the tail end of one second metal strip 6 between the two first metal strips 1 (i.e., the head end and the tail end of each second metal strip 6 are respectively electrically coupled to the head end of one first metal strip and the tail end of the other first metal strip in any adjacent two first metal strips adjacent to the second metal strip), so that the plurality of first metal strips 1 and the plurality of second metal strips 6 form a hollow inductor structure around the fluid cavity;

a liquid inlet 51 and a liquid outlet 52 formed at both ends of the photoresist 2 in the first direction, and in liquid communication with the fluid cavity 3.

Figure 2:
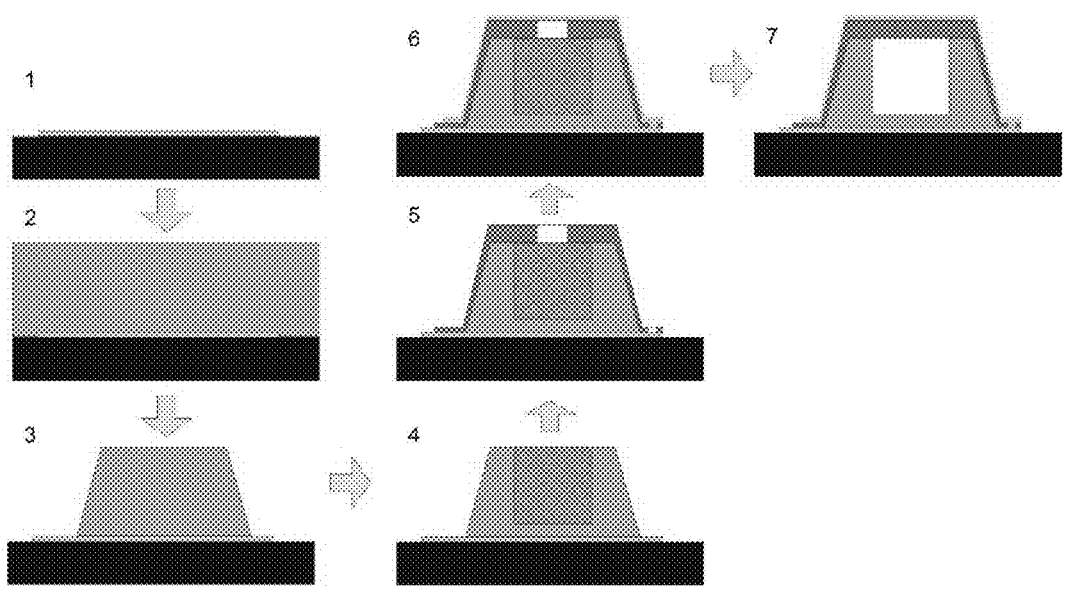
FIG. 2 is a schematic diagram of a manufacturing process for a microfluidic device according to an embodiment of the present disclosure.
Figure 3:
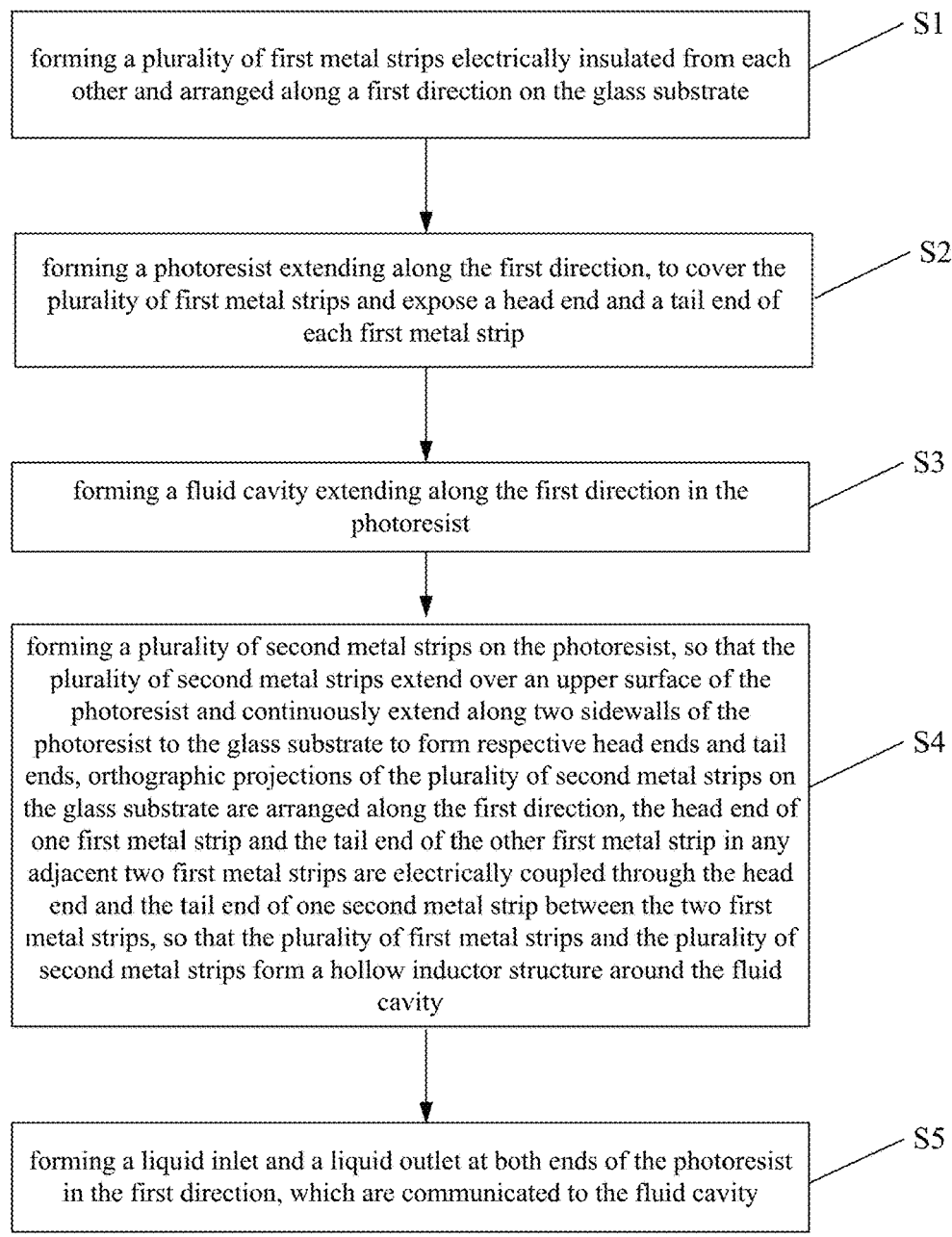
FIG. 3 is a flow chart of a manufacturing method for a microfluidic device according to an embodiment of the present disclosure.

Specifically, FIG. 2 is a schematic diagram of a manufacturing process for a microfluidic device according to an embodiment of the present disclosure, and as shown in FIG. 3, the manufacturing process/method for the microfluidic device in this embodiment includes following steps S1 to S5.

S1, forming a plurality of first metal strips 1 parallel to each other and arranged along a first direction on the glass substrate, wherein the first direction is shown by an arrow in FIG. 1 and is a direction along which the liquid flows in the fluid cavity 3. When each first metal strip 1 is arranged, a tail end of the first metal strip 1 is slightly inclined toward the first direction, that is, an angle between an extending direction of each first metal strip 1 and the first direction is not a right angle. A material of the first metal strip 1 may be Cu/Al/Mo/Ti/Au/Ag or the like or a combination of such metals. The plurality of first metal strips 1 parallel to each other are formed by a patterning manner (e.g., a photolithography etching, a peeling technique, etc.).

S2, coating a photoresist 2 on the glass substrate, wherein the photoresist 2 covers the plurality of first metal strips 1 and has a strip shape, exposing and developing the photoresist 2 in dark, such that an inductor main body with a trapezoidal shape in a front cross-sectional view is formed, and the head end and the tail end of each first metal strip 1 are exposed.

S3, exposing the photoresist 2 inwardly from a middle position at a top of the photoresist 2 in a cuboid pattern, for subsequently forming the fluid cavity 3, wherein a front cross-sectional view of the cuboid is square, and the photoresist 2 is not developed temporarily. A layer of sacrificial colloid 4 is further formed on a surface of the photoresist 2 to cover the inductor main body, wherein the sacrificial colloid 4 and the photoresist 2 are photoresists of different materials, namely the photoresists which can be developed by adopting different developing solutions. The sacrificial colloid 4 at positions covering the head end and the tail end of each first metal strip 1 and the sacrificial colloid 4 at positions, where the liquid inlet 51 and the liquid outlet 52 are to be formed, at two ends of the photoresist 2 in the first direction are exposed and developed, such that the head end and the tail end of each first metal strip 1 are exposed respectively, and the liquid inlet 51 and the liquid outlet 52 are formed, and the cuboid structure of the exposed but undeveloped portion of the photoresist 2 communicated with the liquid inlet 51 and the liquid outlet 52 is formed.

S4, forming a plurality of second metal strips 6 arranged along the first direction and electrically insulated from each other on the sacrificial colloid 4, wherein the plurality of second metal strips 6 extend over an upper surface of the sacrificial colloid 4 and continuously extend along sidewalls of the sacrificial colloid 4 to the glass substrate to form respective head ends and tail ends, all the second metal strips 6 are parallel to each other, and the head end and the tail end of each second metal strip 6 are electrically coupled with the tail end of one first metal strip 1 and the head end of the other first metal strip 1 in the corresponding two first metal strips 1 to which said each second metal strip 6 extends, so that the plurality of first metal strips 1 and the plurality of second metal strips 6 are electrically coupled through the head end and the tail end in an alternative manner, and a metal winding structure wound around the inductor main body is formed.

S5, developing the photoresist 2 exposed in the cuboid pattern for forming the fluid cavity 3, to form the fluid cavity 3 extending along the first direction, removing the photoresist 2 in the cavity to form a hollow inductor structure communicated with outside through the liquid inlet 51 and the liquid outlet 52.

Specifically, in the embodiment of the present disclosure, three first metal strips 1 and three second metal strips 6 are provided to form a winding structure, and the forming process is as follows: the head end 8 of the first one of the second metal strips 6 is used as a first electrode of the hollow inductor structure, the tail end of the first one of the second metal strips 6 is electrically coupled with the head end of the first one of the first metal strips 1, the tail end of the first one of the first metal strips 1 is electrically coupled with the head end of the second one of the second metal strips 6, and so on, the tail end of the $N^{th}$ one of the second metal strips 6 is electrically coupled with the head end of the $N^{th}$ one of the first metal strips 1, and the tail end 9 of the $N^{th}$ one of the first metal strips 1 is used as a second electrode of the hollow inductor structure, where N, n are natural numbers, and satisfy $1 \leq n \leq N-1$, N is a total number of the plurality of first metal strips 1 or a total number of the plurality of second metal strips 6, and is equivalent to three in this embodiment. The plurality of first metal strips 1 extend in a second direction (from upper left to lower right in the figures); the plurality of second metal strips 6 extend along a third direction (from upper right to lower left in the figures), an included angle between the second direction and the third direction is an acute angle, so that the plurality of first metal strips 1 and the plurality of second metal strips 6 are coupled through the head end and the tail end in an alternative manner and surround a surface of the hollow inductor main body to form the winding structure. The hollow inductor manufactured in such way is high in portability and practicability and low in test cost.

As an embodiment of the present disclosure, if a thin film such as a metal is required to be coated in the fluid cavity 3, the cuboid structure to be formed as the fluid cavity 3 in the photoresist 2 may be exposed and then immediately developed to form the fluid cavity 3, then the required metal is deposited and etched to form a pattern, then the sacrificial colloid 4 is covered, and other steps for forming the second metal strips 6 after the sacrificial colloid 4 is formed are unchanged. Thus, operations such as heating (electric heating) reaction substances in the fluid cavity 3 or adding an external electric field, and adding a radio frequency signal and the like can be implemented.

In the above embodiment, a shape of the hollow inductor structure can be provided arbitrarily, and is not limited to providing the photoresist 2 with a strip shape, and the photoresist 2 can be exposed and developed into any desired shape without affecting the purpose of the present disclosure, and the desired exposed shape can be seen visually from the top view of FIG. 1.

Figure 4:
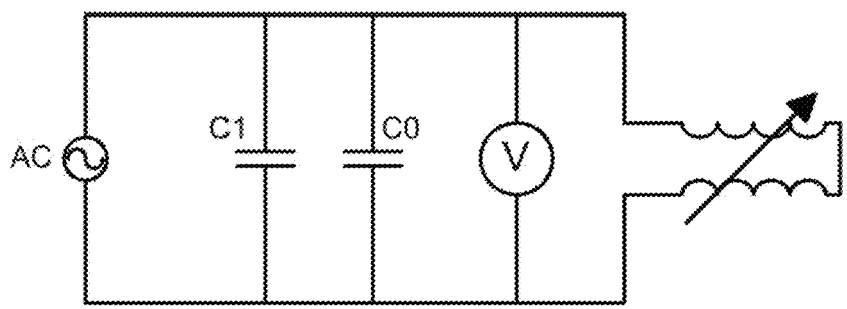
FIG. 4 is a circuit diagram of a system for detecting the number of biomolecules according to an embodiment of the present disclosure.
Figure 5:
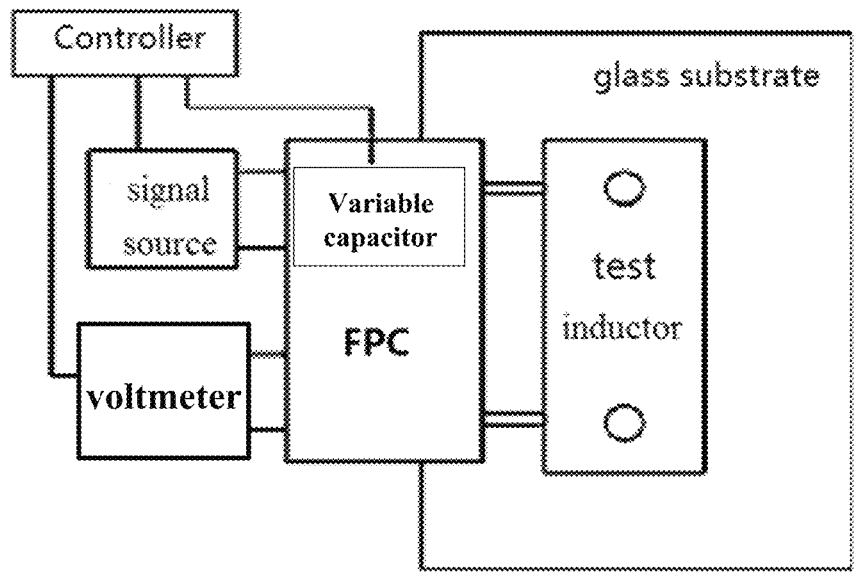
FIG. 5 is a schematic diagram of a structure of a system for detecting the number of biomolecules according to an embodiment of the present disclosure.

FIG. 4 is a circuit diagram of a system for detecting a number of biomolecules according to an embodiment of the present disclosure. In FIG. 4, a variable capacitor C1, a capacitor C0, a voltmeter, and the microfluidic device in the above embodiment are all coupled in parallel and two ends of each of the variable capacitor C1, the capacitor C0, the voltmeter, and the microfluidic device are respectively coupled to positive and negative anodes of an alternating current (AC) power supply. FIG. 5 is a schematic diagram of a structure of a system for detecting a number of biomolecules according to an embodiment of the present disclosure. A first electrode of the hollow inductor structure of the microfluidic device is electrically coupled to a first electrode of the variable capacitor, and a second electrode of the hollow inductor structure is electrically coupled to a second electrode of the variable capacitor; a controller is configured to adjust a frequency of a signal source to cause the hollow inductor structure and the variable capacitor to resonate; the voltmeter is configured to determine whether a resonance is achieved or not through a displayed voltage value across the first electrode and the second electrode of the variable capacitor. The variable capacitor is fabricated on a flexible printed circuit board.

Figure 6:
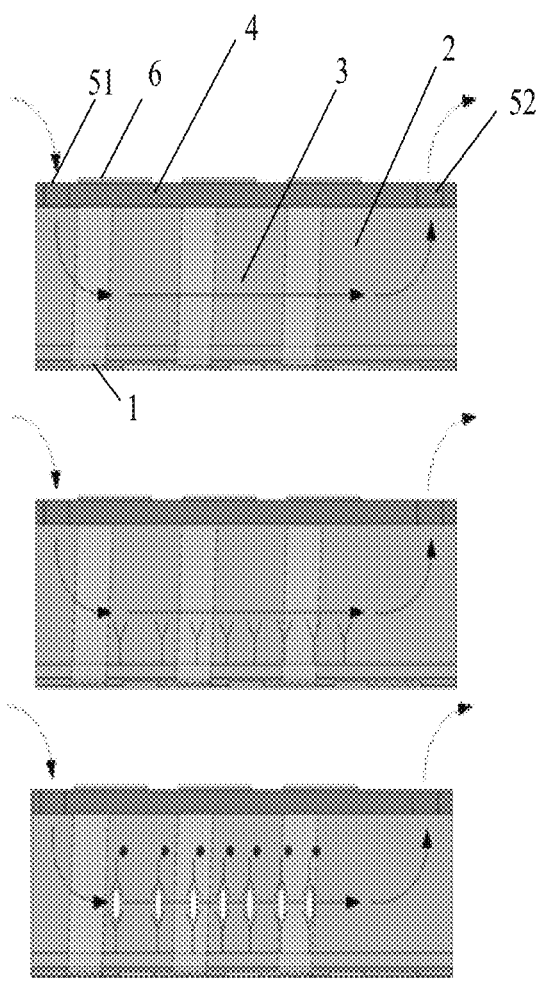
FIG. 6 is a schematic diagram of a method for detecting the number of biomolecules according to an embodiment of the present disclosure.
Figure 7:
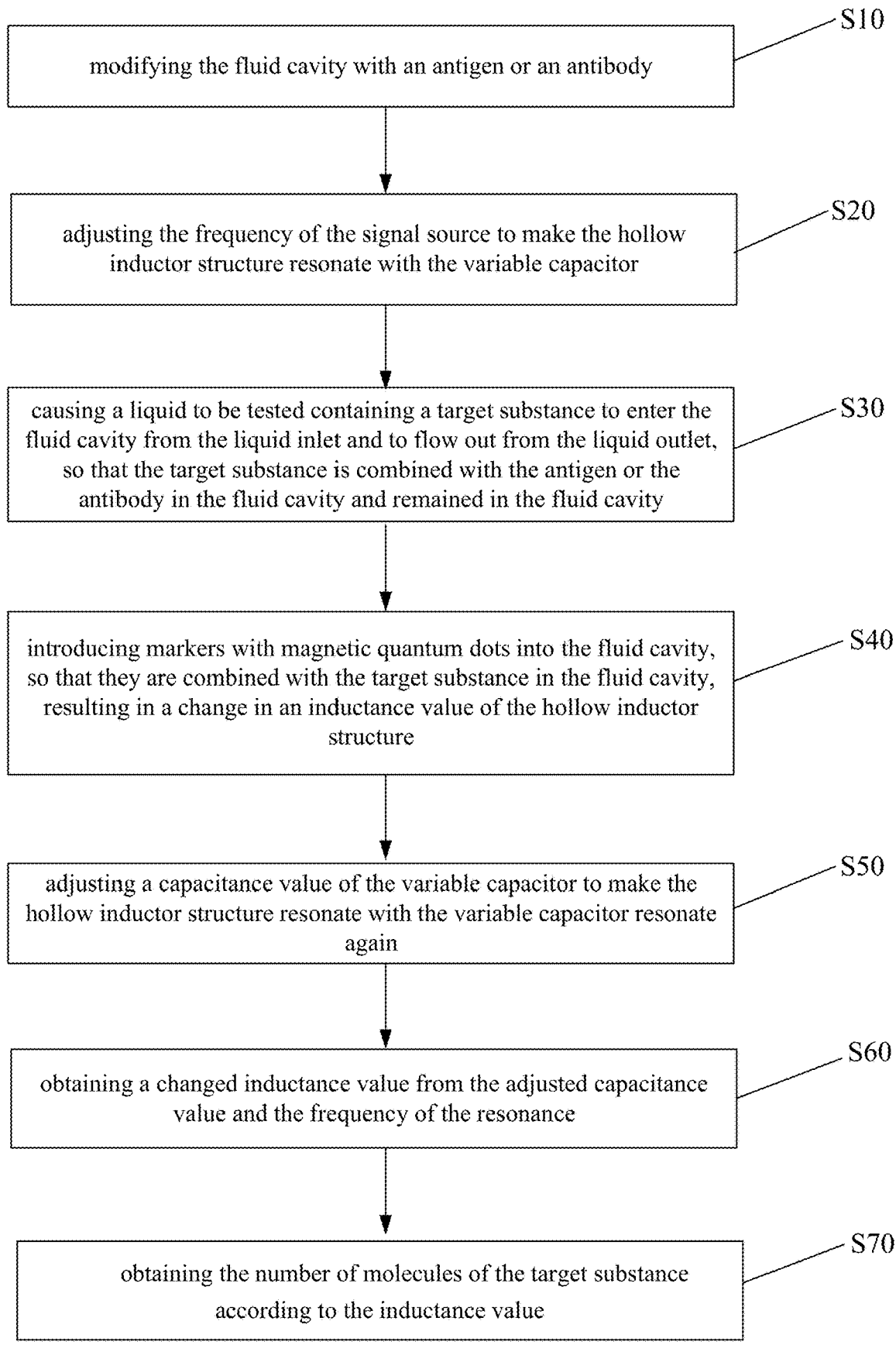
FIG. 7 is a flow chart of a method of performing a detection for the number of biomolecules by a system for detecting the number of biomolecules according to an embodiment of the present disclosure.

FIG. 6 is a schematic diagram of a method for detecting a number of biomolecules according to an embodiment of the present disclosure. As shown in FIG. 6, a first diagram in FIG. 6 shows that an antigen or an antibody is modified in the fluid cavity (S10), and then, the frequency of the signal source is adjusted to resonate the hollow inductor structure and the variable capacitor (S20) while a value of the voltmeter is recorded; a second diagram in FIG. 6 shows that a liquid to be tested containing a target substance enters the fluid cavity from the liquid inlet and flows out from the liquid outlet, and the antigen or the antibody in the fluid cavity is combined with the target substance and remains in the fluid cavity (S30); a third diagram in FIG. 6 shows that markers with magnetic quantum dots (e.g. Fe3O4, etc.) are introduced into the fluid cavity, combined with the target substance previously left in the fluid cavity, a permeability μ in the cavity is increased, resulting in a change of an inductance value in the fluid cavity (S40); then a capacitance value of the variable capacitor is adjusted to cause the hollow inductor structure and the variable capacitor to resonate again (S50), while a value change of the voltmeter is recorded; a changed inductance value is obtained from the adjusted capacitance value and the frequency of the resonance (S60). According to an inductance value formula of a solenoid inductor, $L=(k*solenoid^2*S)/l$, where k is a coefficient depending on a ratio of a radius to a length of a coil of the hollow inductor structure, μ is the permeability, N is the number of turns of the coil, S is a cross-sectional area of the coil, l is the length of the coil, in addition to μ, other parameters are fixed values, the number of the magnetic quantum dots is in direct proportion to the permeability, and the number of molecular particles of the target substance can be obtained by calculating the change of the permeability according to the calculated inductance value (S70). In such way, the value of the number of the molecules measured is accurate, the calculation is simple, and errors are not easy to occur.

As will be appreciated by one of ordinary skill in the art, embodiments of the present application may be provided as a method, a device (apparatus), or a computer program product. Accordingly, the present application may take the form of an entirely hardware embodiment, an entirely software embodiment or an embodiment combining software and hardware aspects. Furthermore, the present application may take the form of a computer program product embodied on one or more computer-usable storage media (including, but not limited to, disk storage, CD-ROM, optical storage, and so forth) having computer-usable program codes embodied therein.

The present application is described with reference to flowcharts and/or block diagrams of the method, the device (apparatus) and the computer program product according to embodiments of the present application. It will be understood that each flow and/or each block of the flowcharts and/or block diagrams, and combinations of flows and/or blocks in the flowcharts and/or block diagrams, can be implemented by computer program instructions. These computer program instructions may be provided to a processor of a general-purpose computer, a special purpose computer, an embedded processor, or any other programmable data processing apparatus to produce a machine, such that the instructions executed by the processor of the computer or any other programmable data processing apparatus, create means for implementing functions specified in one or more flows in the flowchart and/or one or more block or blocks in the block diagram.

These computer program instructions may also be stored in a computer-readable memory that can direct a computer or any other programmable data processing apparatus to function in a particular manner, such that the instructions stored in the computer-readable memory produce an article of manufacture including instruction means which implement functions specified in one or more flows in the flowchart and/or one or more block or blocks in the block diagram.

It should be understood that the above-described embodiments of the present disclosure are examples for clearly illustrating the present disclosure, and are not intended to limit the present disclosure, and that various other modifications and changes may be made on the basis of the above-described embodiments by one of ordinary skill in the art. It is impossible to describe all embodiments here. All obvious modifications and changes derived from the technical solution of the present disclosure are still within the scope of the present disclosure.

What is claimed is:

1. A microfluidic device, comprising:
a glass substrate;
a plurality of first metal strips arranged on the glass substrate in a first direction;
a photoresist extending along the first direction, covering the plurality of first metal strips and exposing a head end and a tail end of each first metal strip;
a fluid cavity extending in the first direction and formed in the photoresist;
a plurality of second metal strips formed on the photoresist, wherein the plurality of second metal strips extend over an upper surface of the photoresist, and continuously extend along sidewalls of the photoresist to the glass substrate, to form respective head ends and tail ends, and wherein orthographic projections of the plurality of second metal strips on the glass substrate are along the first direction, the head end of one first metal strip and the tail end of the other first metal strip in any adjacent two first metal strips are electrically coupled with each other through the head end and the tail end of one second metal strip between the two first metal strips, so that the plurality of first metal strips and the plurality of second metal strips form a hollow inductor structure around the fluid cavity, and the hollow inductor structure is provided with a first electrode and a second electrode for an external connection;
a liquid inlet and a liquid outlet formed at both ends of the photoresist in the first direction, and communicated to the fluid cavity.

2. The device of claim 1, wherein,
in the first direction, the head end of the first one of the plurality of the second metal strips is used as the first electrode of the hollow inductor structure, the tail end of the $n^{th}$ one of the plurality of the second metal strips is electrically coupled with the head end of the $n^{th}$ one of the plurality of the first metal strips, the tail end of the $n^{th}$ one of the plurality of the first metal strips is electrically coupled with the head end of the $(n+1)$th one of the plurality of the second metal strips, the tail end of the $N^{th}$ one of the plurality of the second metal strips is electrically coupled with the head end of the $N^{th}$ one of the plurality of the first metal strips, and the tail end of the $N^{th}$ one of the plurality of the first metal strips is used as the second electrode of the hollow inductor structure,
where N is the number of the plurality of the first metal strips or the plurality of the second metal strips, N and n are natural numbers, and satisfy $1 \leq n \leq N-1$.

3. The device of claim 2, wherein,
the plurality of first metal strips are parallel to each other and extend along a second direction; and
the plurality of second metal strips are parallel to each other and extend along a third direction,
wherein an included angle between the second direction and the third direction is an acute angle.

4. The device of claim 3, wherein each of an included angle between the second direction and the first direction and an included angle between the third direction and the first direction is an acute angle or an obtuse angle.

5. The device of claim 1, wherein the fluid cavity is spaced from the glass substrate by a distance.

6. The device of claim 5, further comprising a sacrificial colloid formed on the photoresist, made of a material different from that of the photoresist, covering the photoresist and extending onto the glass substrate;
the fluid cavity is formed in the photoresist;
the liquid inlet and the liquid outlet are formed in the sacrificial colloid; and
the plurality of second metal strips are formed on an upper surface of the sacrificial colloid.

7. The device of claim 6, wherein,
a cross section of the photoresist perpendicular to an extending direction of the photoresist is of a trapezoidal shape.

8. The device of claim 7, wherein,
the fluid cavity is formed in a middle area of a surface of the photoresist distal to the glass substrate.

9. The device of claim 8, wherein,
a patterned metal film is formed on an inner surface of the fluid cavity.

10. A method for manufacturing a microfluidic device, comprising:
forming a plurality of first metal strips electrically insulated from each other and arranged along a first direction on the glass substrate,
forming a photoresist extending along the first direction, to cover the plurality of first metal strips and expose a head end and a tail end of each first metal strip;
forming a fluid cavity extending along the first direction in the photoresist;
forming a plurality of second metal strips on the photoresist, so that the plurality of second metal strips extend over an upper surface of the photoresist and continuously extend along two sidewalls of the photoresist to the glass substrate to form respective head ends and tail ends, orthographic projections of the plurality of second metal strips on the glass substrate are arranged along the first direction, the head end of one first metal strip and the tail end of the other first metal strip in any adjacent two first metal strips are electrically coupled through the head end and the tail end of one second metal strip between the two first metal strips, so that the plurality of first metal strips and the plurality of second metal strips form a hollow inductor structure around the fluid cavity; and forming a liquid inlet and a liquid outlet at both ends of the photoresist in the first direction, which are communicated to the fluid cavity.

11. The method of claim 10, wherein the forming the fluid cavity extending along the first direction in the photoresist and the forming the plurality of second metal strips on the photoresist comprise:
exposing a part in the photoresist for forming the fluid cavity;
forming a sacrificial colloid covering the photoresist and the exposed head end and the exposed tail end of each first metal strip;
exposing and developing the sacrificial colloid at positions covering the head end and the tail end of each first metal strip and the sacrificial colloid at positions, where the liquid inlet and the liquid outlet are to be formed, at two ends of the photoresist in the first direction, such that the head end and the tail end of each first metal strip are exposed, and the liquid inlet and the liquid outlet are formed,
forming a plurality of second metal strips arranged along the first direction and electrically insulated from each other on the sacrificial colloid, so that the plurality of second metal strips extend over an upper surface of the sacrificial colloid and continuously extend along sidewalls of the sacrificial colloid to the glass substrate to form respective head ends and tail ends, and the head end and the tail end of each second metal strip are electrically coupled with the tail end of one first metal strip and the head end of the other first metal strip in corresponding two first metal strips to which said each second metal strip extends,
developing the photoresist at the exposed position for forming the fluid cavity, to form the fluid cavity extending along the first direction, wherein a hollow inductor structure is formed by the plurality of first metal strips and the plurality of second metal strips surrounding the fluid cavity.

12. The method of claim 10, wherein the forming the fluid cavity extending along the first direction in the photoresist and the forming the plurality of second metal strips on the photoresist comprise:
exposing and developing a part in the photoresist for forming the fluid cavity, to form the fluid cavity extending along the first direction;
forming a patterned metal film in the fluid cavity;
forming a sacrificial colloid covering the photoresist and the exposed head end and the exposed tail end of each first metal strip;
exposing and developing the sacrificial colloid at positions covering the head end and the tail end of each first metal strip and the sacrificial colloid at positions, where the liquid inlet and the liquid outlet are to be formed, at two ends of the photoresist in the first direction, such that the head end and the tail end of each first metal strip are exposed, and the liquid inlet and the liquid outlet are formed,
forming a plurality of second metal strips arranged along the first direction and electrically insulated from each other on the sacrificial colloid, so that the plurality of second metal strips extend over an upper surface of the sacrificial colloid and continuously extend along sidewalls of the photoresist to the glass substrate to form respective head ends and tail ends, and the head end and the tail end of each second metal strip are electrically coupled with the tail end of first metal strip and the head end of the other first metal strip in corresponding two first metal strips to which said each second metal strip extends, wherein a hollow inductor structure is formed by the plurality of first metal strips and the plurality of second metal strips surrounding the fluid cavity.

13. The method of claim 11, wherein the photoresist and the sacrificial colloid are developed with different developing solutions.

14. A system for detecting the number of biomolecules, comprising:
a controller;
a signal source coupled to the controller;
a voltmeter coupled to the controller;
a variable capacitor coupled to the controller, the signal source and the voltmeter;
the microfluidic device according to claim 1,
wherein,
the first electrode of the hollow inductor structure of the microfluidic device is electrically coupled with a first electrode of the variable capacitor, and the second electrode of the hollow inductor structure is electrically connected with a second electrode of the variable capacitor;
the controller is configured to adjust a frequency of the signal source to resonate the hollow inductor structure and the variable capacitor;
the voltmeter is configured to determine whether a resonance is generated or not through a displayed voltage value across the first electrode and the second electrode of the variable capacitor.

15. The system of claim 14, wherein,
the variable capacitor is manufactured on a flexible printed circuit board.

16. A method for detecting the number of biomolecules using the system of claim 14, comprising:
modifying the fluid cavity with an antigen or an antibody;
adjusting the frequency of the signal source to resonate the hollow inductor structure and the variable capacitor;
causing a liquid to be tested containing a target substance to enter the fluid cavity from the liquid inlet and to flow out from the liquid outlet, so that the antigen or the antibody in the fluid cavity is combined with the target substance and remained in the fluid cavity;
introducing markers with magnetic quantum dots into the fluid cavity, so that they are combined with the target substance in the fluid cavity, thereby resulting in a change in an inductance value of the hollow inductor structure;
adjusting a capacitance value of the variable capacitor to resonate the hollow inductor structure and the variable capacitor resonate again;
obtaining a changed inductance value from the adjusted capacitance value and the frequency of the resonance; and
obtaining the number of biomolecules of the target substance according to the inductance value.

17. The method of claim 16, wherein the magnetic quantum dot is $Fe_3O_4$.

18. The device of claim 1, wherein,
the plurality of first metal strips are parallel to each other and extend along a second direction; and
the plurality of second metal strips are parallel to each other and extend along a third direction,
wherein an included angle between the second direction and the third direction is an acute angle.

19. The device of claim 18, wherein each of an included angle between the second direction and the first direction and an included angle between the third direction and the first direction is an acute angle or an obtuse angle.

20. The device of claim 1, further comprising a sacrificial colloid formed on the photoresist, made of a material different from that of the photoresist, covering the photoresist and extending onto the glass substrate;
   the fluid cavity is formed in the photoresist;
   the liquid inlet and the liquid outlet are formed in the sacrificial colloid; and
   the plurality of second metal strips are formed on an upper surface of the sacrificial colloid.

\* \* \* \* \*